US008361513B2

(12) United States Patent
Taniguchi et al.

(10) Patent No.: US 8,361,513 B2
(45) Date of Patent: Jan. 29, 2013

(54) ANTIMICROBIAL ZEOLITE AND ANTIMICROBIAL RESIN COMPOSITION

(75) Inventors: Akio Taniguchi, Nagoya (JP); Kumiko Miyake, Nagoya (JP); Yasuo Kurihara, Nagoya (JP)

(73) Assignee: Sinanen Zeomic Co., Ltd., Aichi (JP)

( * ) Notice: Subject to any disclaimer, the term of this patent is extended or adjusted under 35 U.S.C. 154(b) by 104 days.

(21) Appl. No.: 13/092,221

(22) Filed: Apr. 22, 2011

(65) Prior Publication Data

US 2011/0200523 A1   Aug. 18, 2011

Related U.S. Application Data

(60) Division of application No. 11/648,579, filed on Jan. 3, 2007, now abandoned, which is a continuation of application No. PCT/JP2006/318942, filed on Sep. 25, 2006.

(30) Foreign Application Priority Data

Sep. 27, 2005   (JP) .................................. 2005-280551

(51) Int. Cl.
*A01N 59/16* (2006.01)
*A01N 59/20* (2006.01)

(52) U.S. Cl. ......... 424/618; 424/617; 424/630; 424/641

(58) Field of Classification Search .................. 424/617, 424/618, 630, 641
See application file for complete search history.

(56) References Cited

U.S. PATENT DOCUMENTS

| | | | |
|---|---|---|---|
| 3,393,156 A | 7/1968 | Hansford et al. | |
| 4,775,585 A | 10/1988 | Hagiwara et al. | |
| 4,911,898 A | 3/1990 | Hagiwara et al. | |
| 4,911,899 A | 3/1990 | Hagiwara et al. | |
| 4,938,958 A | 7/1990 | Niira et al. | |
| 5,206,195 A | 4/1993 | Ando et al. | |
| 5,443,812 A * | 8/1995 | Nakajima et al. | 423/700 |
| 6,071,542 A | 6/2000 | Tanimoto et al. | |
| 7,816,295 B2 * | 10/2010 | Liu et al. | 502/60 |

FOREIGN PATENT DOCUMENTS

| | | |
|---|---|---|
| JP | 63-265809 | 11/1988 |
| JP | 64-024860 | 1/1989 |
| JP | 3-218916 | 9/1991 |
| JP | 4-119913 A | 4/1992 |
| JP | 08-127508 | 5/1996 |
| JP | 08-245326 | 9/1996 |
| JP | 10-045410 | 2/1998 |
| JP | 10-095612 | 4/1998 |
| JP | 11-079823 | 3/1999 |
| JP | 11-246213 | 9/1999 |
| JP | 2002-068914 | 8/2002 |
| JP | 11-246212 | 4/2011 |
| KR | 1019970000303 | 10/1998 |
| WO | 96/28028 | 9/1996 |

OTHER PUBLICATIONS

International Search Report dated Nov. 7, 2006 issued in corresponding PCT Application No. PCT/JP2006/318942 with English translation.
Written Opinion of the International Searching Authority dated Nov. 7, 2006 issued in corresponding PCT Application No. PCT/JP2006/318942 with English translation.
Australian Office Action dated Sep. 30, 2009, issued in corresponding Australian Application No. 2006296012.
Korean Office Action dated Jan. 15, 2010, issued in corresponding Korean Application No. 10-2008-7003994, with English translation.
Japanese Official Action issued for corresponding Japanese Patent Application No. 2005-280551, dated May 9, 2011.

* cited by examiner

*Primary Examiner* — John Pak
(74) *Attorney, Agent, or Firm* — Nixon & Vanderhye P.C.

(57) ABSTRACT

The present invention herein provides antimicrobial zeolite which hardly causes any color change with the elapse of time even when it is incorporated into a resin to form an antimicrobial resin composition. The present invention thus relates to antimicrobial zeolite which comprises zeolite whose ion-exchangeable ions are partially or wholly replaced with hydrogen ions and silver ions; and an antimicrobial resin composition which comprises the foregoing antimicrobial zeolite in an amount ranging from 0.05 to 80% by mass.

4 Claims, No Drawings

ANTIMICROBIAL ZEOLITE AND ANTIMICROBIAL RESIN COMPOSITION

This application is a divisional of U.S. patent application Ser. No. 11/648,579, filed Jan. 3, 2007, now abandoned which is a continuation of PCT International Patent Application No. PCT/JP2006/318942 filed Sep. 25, 2006, pending, which claims priority of Japanese Patent Application No. 2005-280551 filed Sep. 27, 2005 the entire contents of which are hereby incorporated by reference in this application.

TECHNICAL FIELD

The present invention relates to antimicrobial zeolite and an antimicrobial composition containing the zeolite and more specifically, to antimicrobial zeolite and an antimicrobial composition and, in particular, an antimicrobial resin composition, which hardly undergo any color change with the elapse of time.

BACKGROUND ART

There has been well known antimicrobial zeolite which comprises a zeolite material whose ion-exchangeable metal ions are replaced with antimicrobial metal ions such as silver, copper and/or zinc ions as well as an antimicrobial composition containing the antimicrobial zeolite. In this respect, it has been known that an antimicrobial resin composition comprising a resin and such antimicrobial zeolite incorporated therein undergoes color change with the elapse of time. As a means for solving the problem that a conventional antimicrobial zeolite of this type undergoes a color change with time, there has been proposed a technique in which silver ions and ammonium ions are incorporated into zeolite (Patent Document 1 specified below).

The antimicrobial zeolite disclosed in this document is in fact a quite excellent antimicrobial agent since it is certainly excellent in its durability of antimicrobial properties observed when allowing it to stand in water or in the air and it does not cause any deterioration even when incorporated into in a resin through kneading operations.

The antimicrobial zeolite disclosed in this document does not suffer from any problem such that it may undergo any extreme color change under the usual use conditions, but it sometimes undergoes a color change with time under severe conditions, for instance, when it is exposed to intensive ultraviolet light rays over a long period of time. The zeolite does not lose its antimicrobial properties peculiar thereto even when it undergoes such a color change, but when adding the antimicrobial zeolite to a product, the latter may often result in discoloration and commercial value of the product may sometimes significantly be damaged depending on the kinds of the product.

Patent Document 1: Japanese Un-Examined Patent Publication Sho 63-265809.

DISCLOSURE OF THE INVENTION

Problems to be solved by the Invention

Accordingly, it is an object of the present invention to provide antimicrobial zeolite which hardly causes any color change with the elapse of time even when it is incorporated into a resin to form an antimicrobial resin composition.

It is another object of the present invention to provide an antimicrobial composition containing the foregoing antimicrobial zeolite and, in particular, an antimicrobial resin composition.

Means for Solving the Problem

The present invention herein provides antimicrobial zeolite and antimicrobial compositions containing the same, as will be detailed below:

1. Antimicrobial zeolite comprising zeolite whose ion-exchangeable ions are partially or wholly replaced with hydrogen ions and silver ions.
2. The antimicrobial zeolite as set forth in the foregoing item 1, wherein it comprises not less than 0.10% by mass of hydrogen ions.
3. An antimicrobial composition comprising antimicrobial zeolite as set forth in the foregoing item 1 or 2 in an amount ranging from 0.05 to 80% by mass.
4. The antimicrobial composition as set forth in the foregoing item 3, wherein it is a resin composition.

EFFECTS OF THE INVENTION

The antimicrobial zeolite of the present invention can be used in wide variety of goods even in those which have been hardly used in combination with the conventional antimicrobial zeolite because of the color change with the elapse of time.

BEST MODE FOR CARRYING OUT THE INVENTION

The present invention will hereunder be described in more detail.

In the present invention, "zeolite" may be either the naturally-occurring ones or the synthetic ones without any restriction. The zeolite is in general an alumino-silicate having a three-dimensional skeletal structure and is represented by the following general formula: $xM_{2/n}O \cdot Al_2O_3 \cdot ySiO_2 \cdot zH_2O$. In the general formula, M represents an ion-exchangeable ion having a valency of n and it is in general a metal ion having a valency of 1 or 2. The suffix x represents the molar number of the corresponding metal oxide, y represents the molar number of silica, and z represents the molar number of water of crystallization.

Specific examples of zeolite usable herein include zeolite A, zeolite X, zeolite Y, zeolite T, zeolite having a high silica content, sodalite, mordenite, analcime, clinoptilolite, chabazite and erionite. However, the present invention is not restricted to these specific ones at all. The ion-exchange capacities of these exemplified zeolite materials are typically as follows: 7 meq/g for zeolite A; 6.4 meq/g for zeolite X; 5 meq/g for zeolite Y; 3.4 meq/g for zeolite T; 11.5 meq/g for sodalite; 2.6 meq/g for mordenite; 5 meq/g for analcime; 2.6 meq/g for clinoptilolite; 5 meq/g for chabazite; and 3.8 meq/g for erionite. Thus, all of these zeolite materials have a high capacity sufficient for allowing ion-exchange with hydrogen ions and silver ions.

The antimicrobial zeolite according to the present invention comprising one of the foregoing zeolite materials, whose ion-exchangeable ions such as sodium ions, calcium ions, potassium ions, magnesium ions and/or iron ions are partially or wholly replaced with hydrogen ions and silver ions. The antimicrobial zeolite of the present invention may likewise comprise, in addition to silver ions, other antimicrobial metal ions and specific examples of such other antimicrobial metal ions include copper, zinc, mercury, lead, tin, bismuth, cadmium, chromium or thallium ions and preferably copper or zinc ions.

The foregoing silver ions and other antimicrobial metal ions are preferably included in the antimicrobial zeolite in an amount ranging from 0.1 to 15% by mass from the viewpoint of the antimicrobial characteristic properties thereof. More preferably, the antimicrobial zeolite comprises silver ions in an amount ranging from 0.1 to 14.9% by mass and copper or zinc ions in an amount ranging from 0.1 to 8% by mass.

On the other hand, it would be suitable to adjust the content of hydrogen ions present in the zeolite to not less than 0.05% by mass and preferably not less than 0.10% by mass from the viewpoint of the effective prevention of the occurrence of any color change of the zeolite. In this connection, the term "% by mass" used herein means that on the basis of the mass of each corresponding substance determined after drying the same at 110° C.

The method for the preparation of the antimicrobial zeolite according to the present invention will then be described in more detail below.

The following two methods can be used for the preparation of the antimicrobial zeolite according to the present invention, which comprises hydrogen and silver ions (and, if necessary, other antimicrobial metal ions), but the present invention is not restricted to these specific methods at all.

The first method comprises the step of bringing a raw zeolite material into contact with a mixed solution containing hydrogen ions, and silver ions (and, if necessary, other antimicrobial metal ions) to thus exchange ion-exchangeable ions present in the zeolite with hydrogen ions and silver ions (and, if necessary, other antimicrobial metal ions). The second method comprises the steps of bringing a raw zeolite material into contact with a mixed solution containing ions capable of generating hydrogen ions through the thermal decomposition of the same (hydrogen ion-generating ions), and silver ions (and, if necessary, other antimicrobial metal ions) to thus exchange ion-exchangeable ions present in the zeolite with hydrogen ion-generating ions, and silver ions (and, if necessary, other antimicrobial metal ions); and heating the resulting product to convert the hydrogen ion-generating ions into hydrogen ions to thus give a zeolite product comprising hydrogen and silver ions (and, if necessary, other antimicrobial metal ions).

According to the first method, zeolite is brought into close contact with a mixed solution prepared in advance and comprising hydrogen ions and silver ions (and, if necessary, other antimicrobial metal ions such as copper ions and/or zinc ions) to thus exchange a part or the whole of the ion-exchangeable ions present in the zeolite with the aforementioned ions. The step for bringing them into contact with one another can be carried out in a batch-wise or continuous method at a temperature ranging from 10 to 70° C. and preferably 40 to 60° C., for a time ranging from 3 to 24 hours and preferably 10 to 24 hours. In this respect, a pH value of the foregoing mixed aqueous solution is suitably adjusted to the range of from 3 to 10 and preferably 5 to 7. This is because the foregoing adjustment of the pH value would permit the prevention of any deposition of, for instance, silver oxide on the zeolite surface and/or within fine pores present therein. In addition, each ion present in the mixed aqueous solution is usually supplied in the form of a salt thereof. In other words, sources of each ion usable herein include, for instance, nitric acid, sulfuric acid, acetic acid, perchloric acid and phosphoric acid for hydrogen ions; silver nitrate, silver sulfate, silver perchlorate, silver acetate, diammine-silver nitrate salt and diammine-silver sulfate salt for silver ions; copper nitrate, copper sulfate, copper perchlorate, copper acetate and potassium tetracyano-cuprate for copper ions; zinc nitrate, zinc sulfate, zinc perchlorate, zinc acetate and zinc thiocyanate for zinc ions; mercury nitrate, mercury perchlorate and mercury acetate for mercury ions; tin sulfate for tin ions; lead sulfate and lead nitrate for lead ions; bismuth chloride and bismuth iodide for bismuth ions; cadmium perchlorate, cadmium sulfate, cadmium nitrate and cadmium acetate for cadmium ions; chromium perchlorate, chromium sulfate, chromium ammonium sulfate and chromium nitrate for chromium ions; and thallium perchlorate, thallium sulfate, thallium nitrate and thallium acetate for thallium ions.

Examples of the foregoing hydrogen ion-generating ions capable of being converted into hydrogen ions through the thermal decomposition thereof and used in the second method are ammonium ions, hydroxyl ammonium ions, various kinds of alkyl ammonium ions, and preferably alkyl ammonium ions whose alkyl group has 1 to 8 carbon atoms such as $NH_3CH_3^+$, $NH_2(CH_3)_2^+$, $NH(CH_3)_3^+$, $N(CH_3)_4^+$, $NH_3(C_2H_5)^+$, $N(C_2H_5)_4^+$, $NH_3(C_3H_7)^+$, $NH_3(C_4H_9)^+$. In this method, the zeolite is brought into contact with a preliminarily prepared mixed aqueous solution containing ammonium ions, hydroxylammonium ions, alkyl ammonium ions and antimicrobial metal ions such as silver ions, copper ions, and/or zinc ions so that the ion-exchangeable ions present on the zeolite are replaced with the foregoing ions. The step for bringing them into contact with one another can be carried out in a batch-wise or continuous method at a temperature ranging from 10 to 70° C. and preferably 40 to 60° C., for a time ranging from 3 to 24 hours and preferably 10 to 24 hours. In this respect, a pH value of the foregoing mixed aqueous solution is suitably adjusted to the range of from 3 to 10 and preferably 5 to 7. This is because the foregoing adjustment of the pH value would ensure the prevention of any deposition of, for instance, silver oxide on the zeolite surface and/or within fine pores present therein.

In addition, each ion present in the mixed aqueous solution is usually supplied in the form of a salt thereof. In other words, sources of each ion usable herein include, for instance, ammonium nitrate, ammonium sulfate, ammonium acetate, ammonium perchlorate, ammonium thiosulfate and ammonium phosphate for ammonium ions; hydroxyammonium hydrochloride for hydroxyammonium ions; methylammonium chloride, dimethylammonium chloride, trimethylammonium chloride, tetramethylammonium chloride, ethylammonium chloride, diethylammonium chloride, triethylammonium chloride, tetraethylammonium chloride, propylammonium chloride and butylammonium chloride for alkylammonium ions; silver nitrate, silver sulfate, silver perchlorate, silver acetate, diammine-silver nitrate salt and diammine-silver sulfate salt for silver ions; copper nitrate, copper sulfate, copper perchlorate, copper acetate and potassium tetracyanocuprate for copper ions; zinc nitrate, zinc sulfate, zinc perchlorate, zinc acetate and zinc thiocyanate for zinc ions; mercury nitrate, mercury perchlorate and mercury acetate for mercury ions; tin sulfate for tin ions; lead sulfate and lead nitrate for lead ions; bismuth chloride and bismuth iodide for bismuth ions; cadmium perchlorate, cadmium sulfate, cadmium nitrate and cadmium acetate for cadmium ions; chromium perchlorate, chromium sulfate, chromium ammonium sulfate and chromium nitrate for chromium ions; and thallium perchlorate, thallium sulfate, thallium nitrate and thallium acetate for thallium ions.

The resulting ammonium ion-containing antimicrobial zeolite is, if necessary, dried and then heated, for instance, at a temperature ranging from 200 to 600° C. over a time ranging from 1 to 24 hours so that the ammonium ions, hydroxyammonium ions and/or alkylammonium ions are heat-decomposed to generate hydrogen ions. As a result, intended antimicrobial zeolite can be obtained, whose ion-exchangeable ions are replaced with hydrogen ions and silver ions.

The contents of, for instance, hydrogen ions and antimicrobial metal ions present in the resulting antimicrobial zeolite can be controlled by appropriately adjusting the concentrations of every ion to be incorporated into the foregoing mixed aqueous solution. For instance, when preparing antimicrobial zeolite comprising ammonium ions and silver ions, the ammonium ion concentration and the silver ion concentration of the foregoing mixed aqueous solution are adjusted to the ranges of from 0.2 to 2.5 M/L for the former and from 0.002 to 0.15 M/L for the latter and a raw zeolite material is added to the mixed aqueous solution in an amount ranging from 500 to 2000 g per liter of the solution to thus bring the zeolite into contact with the solution. Thus, the resulting antimicrobial zeolite appropriately has an ammonium ion content ranging from 0.5 to 5% by mass and a silver ion content ranging from 0.1 to 5% by mass. Moreover, the resulting antimicrobial zeolite may then be heated to give antimicrobial zeolite having a hydrogen ion content ranging from 0.05 to 0.40% by mass and a silver ion content ranging from 0.1 to 5% by mass.

Alternatively, when preparing antimicrobial zeolite further comprising copper ions and zinc ions, the copper and zinc ion concentrations in the foregoing mixed aqueous solution are adjusted to the ranges of from 0.1 to 0.85 M/L for the copper ions and from 0.15 to 1.2 M/L for the zinc ions. As a result, the antimicrobial zeolite thus prepared appropriately has a copper ion content ranging from 0.1 to 8% by mass and a zinc ion content ranging from 0.1 to 8% by mass.

In the present invention, a plurality of aqueous solutions each comprising individual ions may be used in place of a mixed aqueous solution such as those described above and a raw zeolite material is brought into contact with these aqueous solutions one by one so that the zeolite thus undergoes desired ion-exchange reactions. The concentration of each ion present in each corresponding aqueous solution can be determined according to the concentration of each corresponding ion species present in the foregoing mixed aqueous solution.

After the completion of the ion-exchange treatment, the resulting zeolite is sufficiently washed with water and then dried. The zeolite can preferably be dried at a temperature ranging from 105 to 115° C. under ordinary pressure, or at a temperature ranging from 70 to 90° C. under a reduced pressure ranging from 1 to 30 Torr.

In this connection, when the ion-exchangeable ions of zeolite are replaced with, for instance, tin and/or bismuth ions, which are not easily accessible since there have been known only a small number of sources in the form of water-soluble salts, or organic ions, they may be subjected to ion-exchange reactions using solutions thereof in organic solvents such as alcohols or acetone, while preventing the occurrence of any separation of the hardly water-soluble basic salts.

The antimicrobial characteristics of the antimicrobial zeolite according to the present invention thus prepared can be assessed by determining the minimum growth-inhibitory concentrations (MIC) against a variety of general bacteria, fungi and yeast. A test for determining MIC value comprises, for instance, smearing a medium for plate culture, to which an antimicrobial zeolite sample has preliminarily been added in a given concentration, with a bacterium-containing liquid for inoculation; cultivating at 35° C. for 24 hours in case of bacteria or at 25° C. for 4 days in case of fungi and yeast to thus determine the lowest possible concentration required for inhibiting the growth of each microorganism. The resulting lowest concentration is herein defined to be MIC value of each particular zeolite sample.

The present invention also provides an antimicrobial composition and, in particular, an antimicrobial resin composition comprising the foregoing antimicrobial zeolite of the present invention. Examples of resins usable herein are thermoplastic and thermosetting resins such as polyethylene, polypropylene, vinyl chloride resin, ABS resin, polyester, polyvinylidene chloride, polyamide, polystyrene, polyacetal, polyvinyl alcohol, polycarbonate, acrylic resin, polyurethane, phenolic resin, urea resin, melamine resin, epoxy resin, fluoro-resin, rayon, cuprammonium rayon, acetate resin, a variety of elastomers, and naturally occurring and synthetic rubber.

The antimicrobial resin composition of the present invention can be prepared by, for instance, directly incorporating the foregoing antimicrobial zeolite into the resin listed above through kneading or coating the surface of the zeolite with such a resin. The content of the antimicrobial zeolite in the resin composition suitably ranges from 0.05 to 80% by mass and preferably 0.1 to 80% by mass to impart antimicrobial/antifungal/antialgal activities to the resin. In this respect, however, the MIC value of the antimicrobial resin composition can likewise be determined by the same method described above in connection with the antimicrobial zeolite. Furthermore, it is preferred to control the content of the antimicrobial zeolite in the composition to the range of from 0.1 to 3% by mass in order to prevent the occurrence of any color change of the resin.

The foregoing antimicrobial zeolite and antimicrobial composition according to the present invention can be used in a variety of fields.

In the aquatic field, for instance, they can be used as an antimicrobial/antialgal agent for a water purifier, cooling tower water and various kinds of cooling water; and they can likewise be used as an agent for prolonging the life of cut flowers.

In the field of paint and varnish, they may directly be incorporated into various kinds of paints and varnishes such as oil based paints and varnishes, lacquer coatings, varnish coatings, alkyl resin coatings, amino alkyd resin coatings, vinylic resin coatings, acrylic resin coatings, epoxy resin coatings, urethane resin coatings, aqueous emulsion resin coatings, powder coatings, chlorinated rubber coatings and phenolic resin based coatings, or by applying them onto the surface of the coated layer prepared using the foregoing paints to thus impart antimicrobial/antifungal/antialgal activities to the surface of the coated layer.

In the field of construction, the foregoing antimicrobial zeolite and antimicrobial composition according to the present invention can be used by mixing them with, for instance, joint materials, wall materials or tiles; or coating the surface of these materials with them to thus impart antimicrobial/antifungal/antialgal activities to these materials.

In the field of papermaking, they may be used, for instance, by watermarking them into wet tissue paper, paper packaging materials, corrugated fiberboard, paper for spreading under various substances, paper for freshness-keeping, or by coating these paper materials with the antimicrobial zeolite and antimicrobial composition to impart antimicrobial/antifungal/antialgal activities to the materials. Moreover, they may likewise be used, in particular, as a slime-controlling agent (a slime generation-inhibitory agent).

The antimicrobial zeolite according to the present invention can be used not only in the foregoing fields, but also any field which requires the prevention and control of the generation and proliferation of, for instance, general bacteria, fungi, yeast and algae and requires the extinction thereof.

EXAMPLES

The present invention will hereunder be described in more detail with reference to the following Examples.

Example

Preparation of Antimicrobial Zeolite

In this Example, there were used the following 5 kinds of raw zeolite materials: Zeolite A ($Na_2O.Al_2O_3.1.9SiO_2.x\,H_2O$; average particle size: 1.5 μm); Zeolite X ($Na_2O.Al_2O_3.2.3SiO_2.x\,H_2O$; average particle size: 2.5 μm); Zeolite Y ($Na_2O.Al_2O_3.4SiO_2.x\,H_2O$; average particle size: 0.7 μm): naturally occurring mordenite (having a particle size ranging from 150 to 250 mesh); and clinoptilolite (having a particle size ranging from 150 to 250 mesh). In addition, there were used the following four kinds of sources or salts for each ion used in the ion-exchange of these zeolite materials: silver nitrate, copper nitrate, zinc nitrate, and ammonium nitrate.

The following Table 1 shows the kinds of raw zeolite materials, the kinds of salts contained in mixed aqueous solutions and the concentrations thereof used in the preparation of the corresponding samples. As a result, there were prepared samples Nos. 1 to 10 of antimicrobial zeolite.

More specifically, each sample of the antimicrobial zeolite was prepared by adding water to 1 kg of zeolite powder preliminarily dried through heating to a temperature of 110° C. to thus give 1.3 L of a slurry; then degassing the slurry with stirring; and adjusting the pH value of the slurry to the level of 5 to 7 by the addition of a 0.5N aqueous nitric acid solution and water to thus control the total volume of the slurry to 1.8 L. For the purpose of the ion-exchange treatment, the total volume of the slurry was then adjusted to 4.8 L by the addition of 3 L of a mixed aqueous solution containing desired salts at desired concentrations, then the slurry was maintained at a temperature ranging from 40 to 60° C. and the slurry was kept at its equilibrium state over 16 hours with stirring. After the completion of the ion-exchange treatment, the zeolite phase was filtered off, followed by washing the same with water maintained at room temperature or warmed water till all of the excess silver, copper and zinc ions present in the zeolite phase were removed. Then each sample was dried by heating the same at 110° C. to thus give 10 kinds of samples. The samples Nos. 1 to 7 were further heat-treated at 200° C. for 3 hours. The resulting samples were inspected for various characteristic properties and the results thus obtained are likewise listed in the following Table 1. The samples Nos. 1 to 7 are products according to the present invention (Examples; ○: heat-treatment), while the samples Nos. 8 to 10 are products according to Comparative Examples (×: no heat-treatment). The content of hydrogen ions present in each antimicrobial zeolite sample was determined by the calculation on the basis of the value obtained by subtracting the amount of ion-exchanged ions other than hydrogen ions from the theoretical ion-exchange capacity of the zeolite used. In this connection, the samples Nos. 8 to 10 of Comparative Examples were not heat-treated and accordingly, they do not comprise any hydrogen ion.

The contents of metal ions were determined according to the fluorescent X-ray analysis and that of ammonium ions was determined according to the absorption spectrophotometry using indophenol.

TABLE 1

| Sample No. | Kinds of Zeolite | Content in Zeolite (%) $NH_4$ | Ag | Cu | Zn | Yield (g) | Composition of Mixed Aq. Soln. (M/L) $NH_4NO_3$ | $AgNO_3$ | $Cu(NO_3)_2$ | $Zn(NO_3)_2$ | pH of Soln. | Heat-Treatment | $H^+$ ion content (%) |
|---|---|---|---|---|---|---|---|---|---|---|---|---|---|
| 1 | A | 2.5 | 2.5 | — | — | 940 | 3.0 | 0.07 | — | — | 6.8 | ○ | 0.19 |
| 2 | A | 1.2 | 1.0 | — | 14 | 930 | 2.0 | 0.03 | — | 2.0 | 7.2 | ○ | 0.10 |
| 3 | A | 5.0 | 1.0 | 6.1 | — | 910 | 4.5 | 0.03 | 1.2 | — | 7.4 | ○ | 0.39 |
| 4 | X | 1.6 | 2.5 | — | 6.3 | 930 | 2.5 | 0.07 | — | 1.0 | 6.8 | ○ | 0.13 |
| 5 | Y | 1.1 | 1.0 | — | 5.1 | 940 | 1.7 | 0.03 | — | 1.0 | 6.4 | ○ | 0.10 |
| 6 | mordenite | 0.9 | 0.5 | — | 3.0 | 950 | 1.8 | 0.02 | — | 0.7 | 7.5 | ○ | 0.12 |
| 7 | clinoptilolite | 0.8 | 0.1 | 3.0 | — | 940 | 1.8 | 0.02 | 0.7 | — | 7.4 | ○ | 0.13 |
| 8 | A | — | 2.5 | — | — | 930 | — | 0.07 | — | — | 6.9 | × | 0 |
| 9 | A | 2.5 | 2.5 | — | — | 940 | 3.0 | 0.07 | — | — | 6.8 | × | 0 |
| 10 | X | 1.6 | 2.5 | — | 6.3 | 930 | 2.5 | 0.07 | — | 1.0 | 6.8 | × | 0 |

Test Example 1

Test for Antifungal Properties

The antimicrobial properties of the antimicrobial zeolite products prepared in Examples and Comparative Examples were evaluated by the determination of the MIC values thereof against various fungi. The results thus obtained are summarized in the following Table 2.

TABLE 2

| Sample No. | Aspergillus niger NBRC6341 | Fungi belonging to genus Penicillium NBRC6352 | Chaetomium NBRC6347 |
|---|---|---|---|
| 1 | 500 | 500 | 500 |
| 2 | 500 | 500 | 500 |
| 3 | 250 | 500 | 250 |
| 4 | 500 | 500 | 500 |
| 5 | 500 | 500 | 500 |
| 6 | 500 | 500 | 500 |
| 7 | 500 | 500 | 500 |
| 8 | 500 | 500 | 500 |
| 9 | 500 | 500 | 500 |
| 10 | 500 | 500 | 500 |

The data listed in Table 2 clearly indicate that all of the antimicrobial zeolite samples tested have excellent antifungal properties and that the extents thereof are almost identical to one another.

Test Example 2

Test for Antimicrobial Properties

After drying the antimicrobial zeolite samples prepared in Examples and Comparative Examples through heating, each of them was incorporated into a resin through kneading in a kneaded amount of 1% by mass and then the resulting resin composition was injection molded to give a sample of each corresponding antimicrobial resin composition. The resulting samples were evaluated for their antimicrobial properties in an antimicrobially processed good according to the method as specified in JIS Z2801. Bacteria as used herein were *Escherichia coli* and *Staphylococcus aureus*. The following Table 3 shows the kinds of resins used in the molded articles and the results obtained in the foregoing test for evaluating the antimicrobial properties of these articles.

Test Example 3

Test for Color Change

After drying the antimicrobial zeolite samples prepared in Examples and Comparative Examples through heating, each of them was incorporated into a resin through kneading in a kneaded amount of 1% by mass and then the resulting resin composition was injection molded to give a sample of each corresponding antimicrobial resin composition. The resulting samples each were inspected for color change observed after the irradiation thereof with black light rays of 100 W over 100 hours and each color change was evaluated on the basis of the color difference ΔE between the color observed after the foregoing light-irradiation treatment and each color value of the $L^*$-$a^*$-$b^*$ colorimetric system as determined prior to the light-irradiation treatment. The color value was herein determined by placing each sample on a sheet of white Kent paper, while using the Minolta's Color and Color Difference Meter. The following Table 3 shows the kinds of resins used for forming the molded articles and the results obtained in the foregoing tests for evaluating the color change of these articles.

TABLE 3

| Sample No. | Kind of Resin | Results of Tests on Antimicrobial Properties (Values of Antimicrobial Activity) | | Test of Color Change Color Difference (ΔE) |
|---|---|---|---|---|
| | | *Escherichia coli* | *Staphylococcus aureus* | |
| 1 | PE: Petrothene 207R | 3.5 | 3.3 | 0.07 |
| 2 | PP: J707WT | 4.2 | 3.0 | 0.05 |
| 3 | ABS: Styrac 220 | 4.7 | 4.1 | 0.09 |
| 4 | PA: NOVAMID 1010 | 3.3 | 3.6 | 0.04 |
| 5 | PS: TI500A | 4.3 | 4.0 | 0.05 |
| 6 | PE: NUC8009 | 3.2 | 3.7 | 0.06 |
| 7 | PE: NUC8009 | 3.5 | 3.0 | 0.07 |
| 8 | PE: Petrothene 207R | 3.1 | 2.8 | 12.5 |
| 9 | PE: Petrothene 207R | 3.0 | 3.1 | 6.42 |
| 10 | PA: NOVAMID 1010 | 2.8 | 3.0 | 5.41 |

PE: Petrothene 207R (The trade name of a polyethylene product available from Tosoh Corporation);
PP: J707WT (The trade name of a polypropylene available from Grand Polymer K.K.);
ABS: styrac 220 (The trade name of an ABS product available from Asahi Chemical Industry Co., Ltd.);
PA: NOVAMID1010 (The trade name of a polyamide product available from Mitsubishi Engineering Plastics K.K.);
PS: TI500A (The trade name of a polystyrol product available from Dainippon Ink and Chemicals, Inc.); and
PE: NUC8009 (The trade name of a polyethylene product available from Nippon Unicar Co., Ltd.).

The sample No. 7 free of any ammonium ion underwent significant color change. In addition, in the sample Nos. 9 and 10, in which the antimicrobial metal ions were partially exchanged with ammonium ions, the extent of color change was almost reduced by half as compared with that observed for the sample No. 8, but there was still observed distinct color change.

Contrary to this, it could be confirmed that there was not observed any color change in each of the sample Nos. 1 to 7, in which the ammonium ions present therein were converted into hydrogen ions through the heat-treatment described above.

What is claimed is:

1. A method for preparing antimicrobial zeolite whose ion-exchangeable ions are partially or wholly replaced with hydrogen ions and silver ions, which comprises the steps of:
   bringing a raw zeolite material into contact with a mixed solution containing (i) hydrogen ion-generating ions selected from the group consisting of ammonium ions, hydroxyl ammonium ions and alkyl ammonium ions, (ii) silver ions, and (iii) optional other antimicrobial metal ions to exchange ion-exchangeable ions present in the zeolite with said hydrogen ion-generating ions, silver ions, and optional other antimicrobial metal ions; and
   heating the resulting product to a temperature ranging from 200 to 600° C. for a time ranging from 1 to 24 hours to convert the hydrogen-ion generating ions into hydrogen ions to produce a zeolite product comprising 0.05 to 0.40% by mass hydrogen, 0.1 to 5% by mass silver ions, and optional other antimicrobial metal ions.

2. The method according to claim 1, wherein the hydrogen ion-generating ions are ammonium ions.

3. The method according to claim 1, wherein the step of contacting the raw zeolite material with the mixed solution is carried out at a temperature ranging from 10 to 70° C. for a time ranging 3 to 24 hours.

4. The method according to claim 1, wherein the mixed solution has a pH value ranging from 3 to 10.

* * * * *